(12) United States Patent
Brooks et al.

(10) Patent No.: US 7,019,108 B2
(45) Date of Patent: Mar. 28, 2006

(54) METHOD AND COMPOSITION FOR INHIBITION OF ANGIOGENESIS AND TUMOR GROWTH USING COMPOUNDS BASED ON A SEQUENCE WITHIN MMP-2

(75) Inventors: Peter C. Brooks, West Harrison, NY (US); Dorothy Rodriguez, West Harrison, NY (US)

(73) Assignee: University of Southern California, Los Angeles, CA (US)

( * ) Notice: Subject to any disclaimer, the term of this patent is extended or adjusted under 35 U.S.C. 154(b) by 367 days.

(21) Appl. No.: 09/872,165

(22) Filed: Jun. 1, 2001

(65) Prior Publication Data

US 2002/0182215 A1 Dec. 5, 2002

(51) Int. Cl.
*A61K 38/00* (2006.01)

(52) U.S. Cl. ..................................................... 530/300
(58) Field of Classification Search ................ 530/300, 530/317, 327; 514/12
See application file for complete search history.

(56) References Cited

FOREIGN PATENT DOCUMENTS

| WO | WO 97/45137 | * | 12/1997 |
| WO | WO 98/12309 | * | 3/1998 |

OTHER PUBLICATIONS

Stasi et al (Mayo Clin Proc. Apr. 2004;79(4):504-22).*
Lazar et al. Molecular and Cellular Biology 8:1247-1252, 1988.*
Burgess et al., J of Cell Bio. 111:2129-2138, 1990.*
Folkman, J. and Shing, Y., "Angiogenesis," *The Journal of Biological Chemistry*, 267(16): 10931-10934, (1992).
Folkman, J. and Klagsbrun, M., "Angiogenic Factors," *Science*, 235: 442-447, (1987).
Folkman, J., "How is Blood Vessel Growth Regulated in Normal and Neoplastic Tissue?," *CancerResearch*, 46: 467-473, (1986).
Folkman, J., "What is the Evidence that Tumors are Angiogenesis Dependent?," *Journal of the National Cancer Institute*, 82: 4-6, (1989).
Weidner, N., et al., "Tumor Angiogenesis and Metastasis—Correlation in Invasive Breast Carcinoma," *The New England Journal of Medicine*, 324(1): 1-8, (1991).

Varner, J. A., Brooks, P. C., and Cheresh, D. A., "Review: The Integrin $\alpha_v\beta_3$: Angiogenesis and Apoptosis," *Cell Adh. Commun.*, 3, 367-374, (1995).
Gasparini, G. and Harris, A L., "Clinical Importance of the Determination of Tumor Angiogenesis in Breast Carcinoma: Much More than a New Prognostic Tool," *J. Clin. Oncol.*, 13(3): 765-782, (1995).
Greene, T.H. and Wuts, P. G. M., "The Role of Protective Groups in Organic Synthesis," *Protective Groups in Organic Synthesis*, 2nd edition, John Wiley & Sons, New York, 1-9, (1991).
Berge, S.M. et al., "Pharmaceutical Salts," *J. Pharmaceutical Sciences*, 66(1): 1-19, (1997).
Cahn, R.S., et al., "Specification of Molecular Chirality," *Angew, Chem. Int. Ed. Engl.*, 5(4): 385-415, (1966).
IUPAC Commission on Nomenclature of Organic Chemistry, et al., "Nomenclature of $\alpha$-Amino Acids (Recommendations, 1974)," *Biochemistry*, 14(2): 449-462, (1975).
Stewart, J.M. and Young, J. D., "The Chemistry of Solid Phase Peptide Synthesis," *Solid Phase Peptide Synthesis*, W. H. Freeman Co., San Francisco, 1-26, (1963).
Meienhofer, J., "Peptide Synthesis: A Review of the Solid-Phase Method," *Hormonal Proteins and Peptides*, vol. 2, Academic Press, New York, 46-267, (1973).

(Continued)

*Primary Examiner*—Larry R. Helms
*Assistant Examiner*—C. Yaen
(74) *Attorney, Agent, or Firm*—Hogan & Hartson, L.L.P.

(57) ABSTRACT

The present invention provides methods and compositions for inhibiting angiogenesis, tumor growth and treating disease states using a peptide that contains a specific amino acid sequence of matrix metalloproteinase 2 (MMP-2). In one embodiment, the invention provides a peptide, which comprises the amino acid sequence Ile-Phe-Ala-Gly-Asp-Lys-Phe-Trp-Arg, preferably flanked by cysteine residues at the amino and carboxy termini. Additionally, the invention provides compositions for inhibiting angiogenesis or tumor growth or for treating disease states comprising organic and non-peptidic mimetics based on the above amino acid sequence as well as optimized sequences flanking the region of MMP-2 within which the sequence lies. Also provided are methods for detecting angiogenesis, tumorous tissue, metastases, and tumor invasion into a tissue by contacting a composition of the invention with a tissue and methods for screening compositions of the invention.

7 Claims, 5 Drawing Sheets

OTHER PUBLICATIONS

Schroeder, G. and Lupke, K., "The Peptides," vol. 1, *Academic Press*, New York, 1-51; 317-412, (1965).

Ausprunk, D. et al., "Vascularization of Normal and Neoplastic Tissues Grafted to the Chick Chorioallantois," *Am. J. Pathol.*, 79:597-618, (1975).

Ossowski. L., et al., "Experimental Model for Quantitative Study of Metastasis," *Cancer Res.*, 40:2300-2309, (1980).

D'Amato, R.J., et al., "Thalidomide is an Inhibitor of Angiogenesis," *Proc. Natl. Acad. Sci.*, 91:4082-4085, (1994).

Yan, H.-C., et al., "Human/Severe Combined Immunodeficient Mouse Chimeras: An Experimental In Vivo Model System to Study the Regulation of Human Endothelial Cell-Leukocyte Adhesion Molecules," *J. Clin. Invest.*, 91:986-996, (1993).

Poste, G., et al., "Lipid Vesicles as Carriers for Introducing Biologically Active Materials into Cells," *Methods in Cell Biology*, vol. XIV, Academic Press, New York, 33-71, (1975).

* cited by examiner

Effects of Pexstatin (MMP-2 Derived Peptide) on Angiogenesis

No Treatment bFGF

Pexstatin

Control Peptide

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Peptide containing specific amino acid sequence
      of MMP-2

<400> SEQUENCE: 1

Ile Phe Ala Gly Asp Lys Phe Trp Arg
 1               5

<210> SEQ ID NO 2
<211> LENGTH: 11
<212> TYPE: PRT
<213> ORGANISM: Artificial Sequence
<220> FEATURE:
<223> OTHER INFORMATION: Peptide containing specific amino acid sequence
      of MMP-2 flanked by cysteine at the amino and carboxy termini

<400> SEQUENCE: 2

Cys Ile Phe Ala Gly Asp Lys Phe Trp Arg Cys
 1               5                  10
```

METHOD AND COMPOSITION FOR INHIBITION OF ANGIOGENESIS AND TUMOR GROWTH USING COMPOUNDS BASED ON A SEQUENCE WITHIN MMP-2

GOVERNMENT SUPPORT

This invention was made with government support under Contract No. R29CA 74132-01 by the National Cancer Institute.

FIELD OF THE INVENTION

The invention relates generally to the field of medicine, and relates specifically to methods and compositions for inhibiting tumor growth and angiogenesis in a tissue or detecting angiogenesis and tumor growth using compounds based on a specified sequence found within MMP-2.

BACKGROUND

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions, these molecules appear to maintain the microvasculature in a quiescent state (i.e. one of no capillary growth) for prolonged periods which may last for as long as weeks or in some cases, decades. When necessary however (such as during wound repair), these same cells can undergo rapid proliferation and turnover within a 5 day period. (Folkman, J. and Shing, Y., The Journal of Biological Chemistry, 267(16): 10931–10934, and Folkman, J. and Klagsbrun, M., Science, 235: 442–447 (1987)).

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exacerbate an existing pathological condition. For example, ocular neovascularization has been implicated as the most common cause of blindness and dominates approximately 20 eye diseases. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (Folkman, J., Cancer Research, 46: 467–473 (1986), Folkman, J., Journal of the National Cancer Institute, 82: 4–6 (1989)). It has been shown, for example, that tumors which enlarge to greater than 2 mm, must obtain their own blood supply and do so by inducing the growth of new capillary blood vessels. Once these new blood vessels become embedded in the tumor, they provide a means for tumor cells to enter the circulation and metastasize to distant sites, such as liver, lung or bone (Weidner, N., et al., The New England Journal of Medicine, 324(1): 1–8 (1991)).

Because tumor growth and metastasis impacts a large number of people each year (it is estimated that well over 600,000 new cases of cancer will be diagnosed in the coming year in the United States alone. Varner, J. A., Brooks, P. C., and Cheresh, D. A. (1995) *Cell Adh. Commun.* 3, 367–374), compositions and treatment methods for treating these diseases have great utility. From the foregoing it is clear that blocking angiogenesis may be efficacious in slowing tumor growth and treating various other diseases. In fact, there is ample evidence supporting the contention that blocking tumor neovascularization can inhibit tumor growth in various animal models, and human clinical data is beginning to support this contention as well (Varner, J. A., Brooks, P. C., and Cheresh, D. A. (1995) *Cell Adh. Commun.* 3, 367–374).

Although several angiogenesis inhibitors are currently under development for use in treating angiogenic diseases (Gasparini, G. and Harris, A. L., J Clin Oncol 13(3): 765–782, (1995)), there are disadvantages associated with several of these compounds. For example, suramin is a potent angiogenesis inhibitor, but causes (at doses required to reach anti-tumor activity) severe systemic toxicity in humans. Other compounds, such as retinoids, interferons and antiestrogens are safe for human use but have only a weak anti-angiogenic effect. Still other compounds may be difficult or costly to make. Similarly, although many investigators have focused on growth factors and cytokines that initiate angiogenesis (Varner et al. 1995; Blood and Zetter 1990; Weidner et al. 1992; Weidner et al. 1991; Brooks et al. 1995; Brooks et al. 1994; Brooks et al. 1997), there is a redundancy in the number of distinct growth factors and cytokines which have the capacity to stimulate angiogenesis. Therefore, the therapeutic benefit of blocking a single cytokine may have only limited benefit due to this redundancy.

Accordingly, what is needed is the invention of other anti-angiogenic targets and methods for inhibiting angiogenesis. Short peptides are relatively simple to make and represent a cost effective method of treating disease states in which angiogenesis plays a role and in designing targeted inhibitors of angiogenesis.

SUMMARY

The present invention provides methods and compositions for inhibiting angiogenesis and tumor growth using matrix metalloproteinases (MMP), which play a role in the proteolytic remodeling of the extracellular matrix (ECM). Specifically, the present invention provides a novel composition and method for inhibiting angiogenesis based on a fragment of MMP-2.

One particular aspect of the invention provides compositions for inhibiting angiogenesis comprising a peptide that contains a specific amino acid sequence of MMP-2. In its principal embodiment, the present invention provides a peptide, which comprises the following amino acid sequence:

SEQ. ID. NO.: 1—Ile-Phe-Ala-Gly-Asp-Lys-Phe-Trp-Arg

Alternatively, the above sequence may be flanked by other amino acids. For, example, the 9 amino acid sequence may be flanked by cysteine residues at the amino and carboxy termini as below:

SEQ. ID. NO.: 2—Cys-Ile-Phe-Ala-Gly-Asp-Lys-Phe-Trp-Arg-Cys

Additionally, the invention provides compositions for inhibiting angiogenesis or tumor growth comprising organic and non-peptidic mimetics based on the above amino acid sequence as well as optimized sequences flanking the region of MMP-2 within which the sequence lies.

Another aspect of this invention provides compositions for inhibiting angiogenesis comprising agonists of a site defined by a specific amino acid sequence of MMP-2. Further, the invention provides antagonists for inhibiting angiogenesis directed specifically to a specific site within MMP-2. Such antagonists may include organic and peptidic or non-peptidic mimetics of the epitope.

In yet another embodiment, the present invention provides a composition for the treatment of a disease selected from the group consisting of cancer, arthritis, psoriasis, angiogenesis of the eye associated with infection or surgical intervention, macular degeneration and diabetic retinopathy comprising a peptide as defined above in combination with a pharmaceutically acceptable carrier.

Yet another aspect of the invention involves methods of inhibiting angiogenesis comprising contacting a tissue with the above compositions. The tissue to be treated can be any tissue in which inhibition of angiogenesis is desirable, such as diseased tissue where neovascularization is occurring. Exemplary tissues include inflamed tissue, solid tumors, metastases, tissues undergoing restenosis, and the like. The invention also provides a treatment method for a disease selected from the group consisting of cancer, arthritis, macular degeneration and diabetic retinopathy comprising administering to the patient a therapeutically effective amount of a peptide as defined above.

Methods also are provided for detecting angiogenesis, tumorous tissue, metastases, and tumor invasion into a tissue by contacting a composition of the invention with a tissue.

The invention also provides methods for screening compositions of the invention.

Throughout the patent specification,
1. SEQ. ID. NO.:1 is the following sequence: Ile-Phe-Ala-Gly-Asp-Lys-Phe-Trp-Arg
2. Pexstatin or SEQ. ID. NO.:2 refers to a peptide, which has the sequence:
Cys-Ile-Phe-Ala-Gly-Asp-Lys-Phe-Trp-Arg-Cys

DETAILED DESCRIPTION OF THE INVENTION

Figure 1:
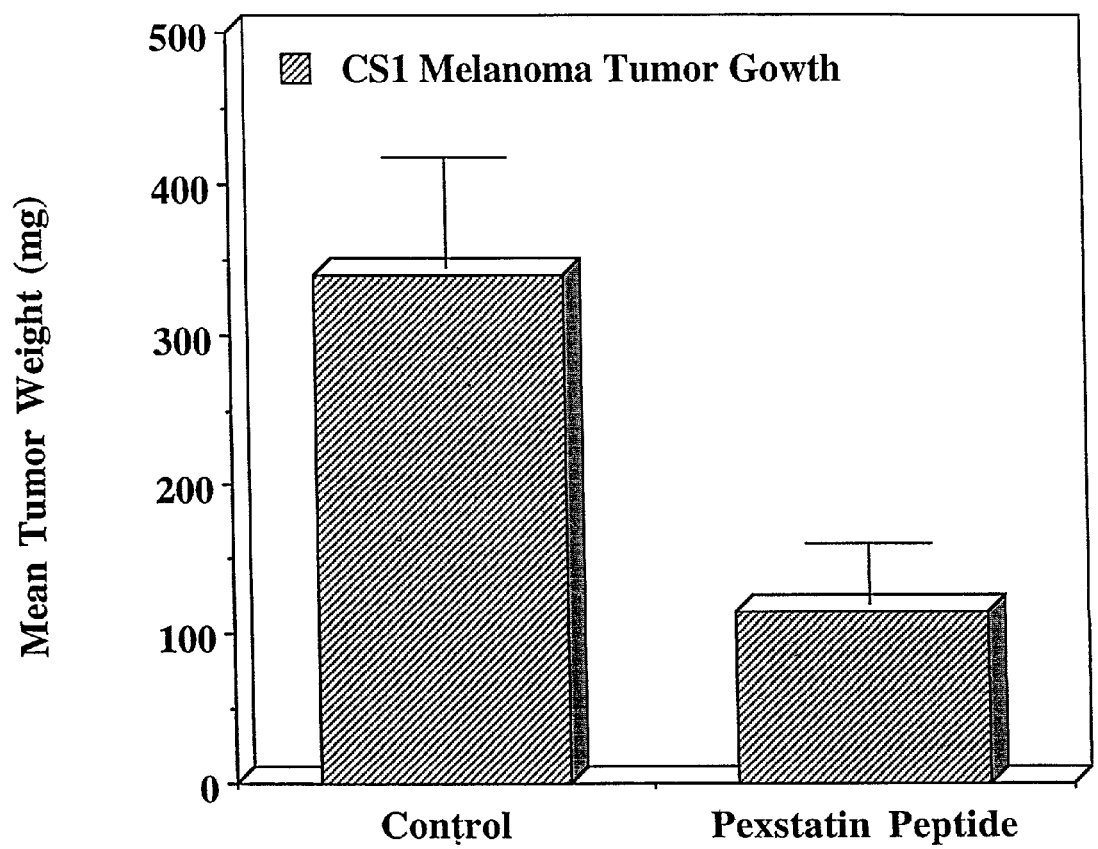
FIG. 1 shows the effects of systemic administration of Pexstatin on melanoma tumor growth in the chick embryo.

In the physiological state, the synthesis of connective tissues is in dynamic equilibrium with the degradation of the extracellular matrix. That degradation is due, in part, to matrix metalloproteases, a family of proteases (enzymes) involved in the degradation and remodeling of connective tissues. Members of this family of endopeptidase enzymes are secreted as proenzymes from various cell types that reside in or are associated with connective tissue, such as fibroblasts, monocytes, macrophages, endothelial cells, and invasive or metastatic tumor cells. MMP expression is stimulated by growth factors and cytokines in the local tissue environment, where these enzymes act to specifically degrade protein components of the extracellular matrix, such as collagen, proteoglycans (protein core), fibronectin and laminin. These ubiquitous extracellular matrix components are present in the linings of joints, interstitial connective tissues, basement membranes and cartilage. The MMPs share a number of properties, including zinc and calcium dependence, secretion as zymogens, and 40–50% amino acid sequence homology.

Excessive degradation of extracellular matrix by MMPs is implicated in the pathogenesis of many diseases of both chronic and acute nature. For example, numerous studies, as reviewed in Exp. Opin. Invest. Drugs, 5, 323–335, (1996), have established that expression and activation of MMPs are critical events in tumor growth, invasion and metastasis. In addition, MMP activity has been found to be required for angiogenesis, which is necessary for tumor growth as well as for other pathological conditions such as macular degeneration.

The members of this family of enzymes include, but ARE not limited to, collagenases (MMP-1), gelatinases or collagenases of type IV (MMP-2, MMP-9), matrilysin (MMP-7, PUMP-1), and stromelysins (MMP-3).

Of particular interest here is the gelatinase MMP-2.

Definitions

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "N-protecting group", as used herein, refers to an easily removable group which is known in the art to protect an amino group against undesirable reaction during synthetic procedures and to be selectively removable. The use of N-protecting groups is well known in the art for protecting groups against undesirable reactions during a synthetic procedure and many such protecting groups are known, cf, for example, T. H. Greene and P. G. M. Wuts, Protective Groups in Organic Synthesis, 2nd edition, John Wiley & Sons, New York (1991). Examples of N-protecting groups include, but are not limited to, acyl groups including acetyl, trifluoroacetyl, acylisothiocyanate, aminocaproyl, benzoyl and the like, and acyloxy groups, including t-butyloxycarbonyl (BOC) and carbobenzyloxy, and the like.

By "pharmaceutically acceptable salt" it is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

Unless indicated otherwise by a "D" prefix, the stereochemistry of the I-carbon of the amino acids and aminoacyl residues in peptides described in this specification and the appended claims is the natural or "L" configuration. The Cahn-Ingold-Prelog "R" and "S" designations are used to specify the stereochemistry of chiral centers in certain of the acyl substituents at the N-terminus of the peptides of this invention. The designation "R,S" is meant to indicate a racemic mixture of the two enantiomeric forms. This nomenclature follows that described in R. S. Cahn, et al., Angew. Chem. Int. Ed. Engl., 5, 385–415 (1966).

For the most part, the names on naturally-occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of I-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader by the following.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8) Tyr (−2.3); Phe (−2.5); and Trp (−3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

Compounds of the Invention: Peptides

In accordance with the present invention, it has been discovered that a specific region of the matrix metalloproteinase-2 (MMP-2) defined by amino acid positions 582–590 potently inhibits angiogenesis and tumor growth.

Based on the above finding, the invention provides a novel peptide with SEQ ID NO:1 and a novel eleven amino acid peptide, Pexstatin, with SEQ ID NO: 2 for inhibiting angiogenesis and tumor growth. As the examples below demonstrate, these peptides potently inhibit angiogenesis and tumor growth in vivo. Thus, the compounds of the invention, including but not limited to those specified in the examples, possess anti-angiogenic activity.

The polypeptides of the present invention may be synthesized by any of the techniques that are known to those skilled in the art. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Acacemic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

One method of preparing compounds of the present invention involves solid phase peptide synthesis. In this method, the alpha-amino function is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, (I,I) dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is preferred.

Particularly preferred side chain protecting groups are, for side chain amino groups as in lysine and arginine: 2,2,5,7, 8-pentamethylchroman-6-sulfonyl (pmc), nitro, p-toluenesulfonyl, 4-methoxybenzenesulfonyl, Cbz, Boc, and adamantyloxycarbonyl; for tyrosine: benzyl, o-bromobenzyloxycarbonyl, 2,6-dichlorobenzyl, isopropyl, t-butyl (t-Bu), cyclohexyl, cyclopenyl and acetyl (Ac); for serine: t-butyl, benzyl and tetrahydropyranyl; for histidine: trityl, benzyl, Cbz, p-toluenesulfonyl and 2,4-dinitrophenyl; for tryptophan: formyl.

In the solid phase peptide synthesis method, the C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of C-terminal carboxy peptides is 4-hydroxymethylphenoxymethylcopoly(styrene-1% divinylbenzene). The preferred solid support for C-terminal amide peptides is 4-(2',4'-dimethoxyphenyl-Fmoc-aminomethyl) phenoxyacetamidoethyl resin available from Applied Biosystems.

The C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris (dimethylamino)phosphoniumhexafluorophosphate (BOP) or bis(2-oxo-3-oxazolidinyl)phosphine chloride (BOPCl), mediated coupling for from about 1 to about 24 hours at a temperature of between 100 and 50° C. in a solvent such as dichloromethane or DMF. When the solid support is 4-(2',4'-dimethoxyphenyl-Fmoc-aminomethyl)phenoxyacetamidoethyl resin, the Fmoc group is cleaved with a secondary amine, preferably piperidine, prior to coupling with the C-terminal amino acid as described above. The preferred method for coupling to the deprotected 4-(2',4'-dimethoxyphenyl-Fmoc-aminomethyl)phenoxyacetamidoethyl resin is O-benzotriazol-1-yl-N,N,N',N'-tetramethyluronium-hexafluorophosphate (HBTU, 1 equiv.) and 1-hydroxybenzotriazole (HOBT, 1 equiv.) in DMF.

The coupling of successive protected amino acids can be carried out in an automatic polypeptide synthesizer as is well known in the art. In one embodiment, the α-amino function in the amino acids of the growing peptide chain are protected with Fmoc. The removal of the Fmoc protecting group from the N-terminal side of the growing peptide is accomplished by treatment with a secondary amine, preferably piperidine. Each protected amino acid is then introduced in about 3-fold molar excess and the coupling is preferably carried out in DMF. The coupling agent is normally O-benzotriazol-1-yl-N,N,N',N'-tetramethyluroniumhexafluorophosphate (HBTU, 1 equiv.) and 1-hydroxybenzotriazole (HOBT, 1 equiv.).

At the end of the solid phase synthesis, the polypeptide is removed from the resin and deprotected, either successively or in a single operation. Removal of the polypeptide and deprotection can be accomplished in a single operation by treating the resin-bound polypeptide with a cleavage reagent, for example thianisole, water, ethanedithiol and trifluoroacetic acid.

In cases wherein the C-terminus of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above.

The fully deprotected peptide is purified by a sequence of chromatographic steps employing any or all of the following types: ion exchange on a weakly basic resin in the acetate form; hydrophobic adsorption chromatography on underivitized polystyrene-divinylbenzene (for example, AMBERLITE.RTM. XAD); silica gel adsorption chromatography; ion exchange chromatography on carboxymethylcellulose; partition chromatography, e.g. on SEPHADEX.RTM. G-25, LH-20 or countercurrent distribution; high performance liquid chromatography (HPLC), especially reverse-phase HPLC on octyl- or octadecylsilyl-silica bonded phase column packing.

Angiogenesis Assays

The compounds of the invention can be assayed for their ability to modulate angiogenesis in a tissue. Any suitable assay known to one of skill in the art can be used to monitor such effects. Several such techniques are described herein.

For example, one assay measures angiogenesis in the chick chorioallantoic membrane (CAM) and is referred to as the CAM assay. The CAM assay has been described in detail by others, and further has been used to measure both angiogenesis and neovascularization of tumor tissues. See Ausprunk et al., *Am. J Pathol.*, 79:597–618 (1975) and Ossonski et al., *Cancer Res.*, 40:2300–2309 (1980).

The CAM assay is a well recognized assay model for in vivo angiogenesis because neovascularization of whole tissue is occurring, and actual chick embryo blood vessels are growing into the CAM or into the tissue grown on the CAM.

As demonstrated herein, the CAM assay illustrates inhibition of neovascularization based on both the amount and extent of new vessel growth. Furthermore, it is easy to monitor the growth of any tissue transplanted upon the CAM, such as a tumor tissue. Finally, the assay is particularly useful because there is an internal control for toxicity in the assay system. The chick embryo is exposed to any test reagent, and therefore the health of the embryo is an indication of toxicity.

A second assay that measures angiogenesis is the in vivo rabbit eye model and is referred to as the rabbit eye assay. The rabbit eye assay has been described in detail by others, and further has been used to measure both angiogenesis and neovascularization in the presence of angiogenic inhibitors such as thalidomide. See D'Amato et al. (1994) *Proc. Natl. Acad. Sci.* 91:4082–4085.

The rabbit eye assay is a well recognized assay model for in vivo angiogenesis because the neovascularization process, exemplified by rabbit blood vessels growing from the rim of the cornea into the cornea, is easily visualized through the naturally transparent cornea of the eye. Additionally, both the extent and the amount of stimulation or inhibition of neovascularization or regression of neovascularization can easily be monitored over time.

Finally, the rabbit is exposed to any test reagent, and therefore the health of the rabbit is an indication of toxicity of the test reagent.

A fourth assay measures angiogenesis in the chimeric mouse:human mouse model and is referred to as the chimeric mouse assay. The assay has been described in detail by others to measure angiogenesis, neovascularization, and regression of tumor tissues. See Yan, et al. (1993) *J. Clin. Invest.* 91:986–996.

The chimeric mouse assay is a useful assay model for in vivo angiogenesis because the transplanted skin grafts closely resemble normal human skin histologically and neovascularization of whole tissue is occurring wherein actual human blood vessels are growing from the grafted human skin into the human tumor tissue on the surface of the grafted human skin. The origin of neovascularization into the human graft can be demonstrated by immunohistochemical staining of the neovasculature with human-specific endothelial cell markers.

The chimeric mouse assay demonstrates regression of neovascularization based on both the amount and extent of regression of new vessel growth. Furthermore, it is easy to monitor effects on the growth of any tissue transplanted upon the grafted skin, such as a tumor tissue. Finally, the assay is useful because there is an internal control for toxicity in the assay system. Because the chimeric mouse is exposed to a test reagent, the health of the mouse is an indication of toxicity.

Therapeutic Compositions

The compounds of the invention may be used in combination with other compositions and procedures for the treatment of diseases. For example, a tumor may be treated conventionally with surgery, radiation or chemotherapy combined with a peptide of the present invention and then a peptide of the present invention may be subsequently administered to the patient to extend the dormancy of micrometastases and to stabilize and inhibit the growth of any residual primary tumor. Additionally, the compounds of the invention may be combined with pharmaceutically acceptable excipients, and optionally sustained-release matrices, such as biodegradable polymers, to form therapeutic compositions.

A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho) esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

When used in the above or other treatments, a therapeutically effective amount of one of the compounds of the present invention may be employed in pure form or, where such forms exist, in pharmaceutically acceptable salt form. By a "therapeutically effective amount" of the compound of the invention is meant a sufficient amount of the compound to treat an angiogenic disease, (for example, to limit tumor growth or to slow or block tumor metastasis) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxy-ethansulfonate (isethionate), lactate, maleate, methanesulfonate, nicotinate, 2-naphthalenesulfonate, oxalate, pamoate, pectinate, persulfate, 3-phenylpropionate, prcrate, pivalate, propionate, succinate, tartrate, thiocyanate, phosphate, glutamate, bicarbonate, p-toluenesulfonate and undecanoate. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as maleic acid, succinic acid and citric acid. Other salts include salts with alkali metals or alkaline earth metals, such as sodium, potassium, calcium or magnesium or with organic basis. Preferred salts of the compounds of the invention include phosphate, tris and acetate.

Alternatively, a compound of the present invention may be administered as pharmaceutical compositions containing the compound of interest in combination with one or more pharmaceutically acceptable excipients. A pharmaceutically acceptable carrier or excipient refers to a non-toxic solid, semi-solid or liquid filler, diluent, encapsulating material or formulation auxiliary of any type.

Pharmaceutical compositions for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent It is preferred to use the solid anionic surface active agent in the form of a sodium salt.

A further form of topical administration is to the eye. A compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds of the invention may be injected directly into the vitreous and aqueous humour.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

While the compounds of the invention can be administered as the sole active pharmaceutical agent, they may also be used in combination with one or more agents which are conventionally administered to patients for treating angiogenic diseases. For example, the compounds of the invention are effective over the short term to make tumors more sensitive to traditional cytotoxic therapies such as chemicals and radiation. The compounds of the invention also enhance the effectiveness of existing cytotoxic adjuvant anti-cancer therapies. The compounds of the invention may also be combined with other antiangiogenic agents to enhance their effectiveness, or combined with other antiangiogenic agents and administered together with other cytotoxic agents. In particular, when used in the treatment of solid tumors, compounds of the invention may be administered with IL-12, retinoids, interferons, angiostatin, endostatin, thalidomide, thrombospondin-1, thrombospondin-2, captopryl, anti-neoplastic agents such as alpha inteferon, COMP (cyclophosphamide, vincristine, methotrexate and prednisone), etoposide, MBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like as well as with rediation.

It will be understood that agents which can be combined with the compound of the present invention for the inhibition, treatment or prophylaxis of angiogenic diseases are not limited to those listed above, but include in principle any agents useful for the treatment or prophylaxis of angiogenic diseases.

Methods for Inhibition of Angiogenesis and Disease Treatment

The invention provides for a method for the inhibition of angiogenesis in a tissue, and thereby inhibiting events in the tissue which depend upon angiogenesis. Generally, the method comprises administering to the tissue a composition comprising an angiogenesis-inhibiting amount of a compound of the invention, e.g., Pexstatin.

As described earlier, angiogenesis includes a variety of processes involving neovascularization of a tissue including "sprouting", vasculogenesis, or vessel enlargement, all of which angiogenesis processes involve disruption of extracellular matrix collagen in blood vessels. With the exception of traumatic wound healing, corpus leuteum formation and embryogenesis, it is believed that the majority of angiogenesis processes are associated with disease processes and therefore the present therapeutic methods are useful for treating diseases.

As angiogenesis inhibitors, compounds of the invention, such as Pexstatin, are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints'; angiofibroma; and wound granulation. Other uses include the treatment of diseases characterized by excessive or abnormal stimulation of endothelial cells, including but not limited to intestinal adhesions, Crohn's disease, atherosclerosis, scleroderma, and hypertrophic scars, i.e. keloids. Another use is as a birth control agent, by inhibiting ovulation and establishment of the placenta. The compounds of the invention are also useful in the treatment of diseases that have angiogenesis as a pathologic consequence such as cat scratch disease (Rochele ninalia quintosa) and ulcers (Helicobacter pylori). The compounds of the invention are also useful to reduce bleeding by administration prior to surgery, especially for the treatment of resectable tumors.

The methods of the present invention are effective in part because the therapy is highly selective for angiogenesis and not other biological processes. Moreover, the compounds of the invention are highly potent suggesting that they may have therapeutic benefits at low concentrations.

Any of a variety of tissues, or organs comprised of organized tissues, can support angiogenesis in disease conditions including skin, muscle, gut, connective tissue, joints, bones and the like tissue in which blood vessels can invade upon angiogenic stimuli. Tissue, as used herein, also encompasses all bodily fluids, secretions and the like, such as serum, blood, cerebrospinal fluid, plasma, urine, synovial fluid, vitreous humor.

Thus, in one embodiment, a tissue to be treated is an inflamed tissue and the angiogenesis to be inhibited is inflamed tissue angiogenesis where there is neovascularization of inflamed tissue. In this class the method contemplates inhibition of angiogenesis in arthritic tissues, such as in a patient with chronic articular rheumatism, in immune or non-immune inflamed tissues, in psoriatic tissue and the like.

The patient treated by the many embodiments of the present invention is desirably a human patient, although it is to be understood that the principles of the invention indicate that the invention is effective with respect to all mammals, which are intended to be included in the term "patient". In this context, a mammal is understood to include any mammalian species in which treatment of diseases associated with angiogenesis is desirable, particularly agricultural and domestic mammalian species. Such a patient can be, for example, a pig, a cow, a horse, a goat, a sheep, a mule, a donkey, a dog, a cat, a rabbit, a mouse and a rat.

In another related embodiment, a tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, Kaposi's Sarcoma and the like tissues. Exemplary tumor tissue angiogenesis, and inhibition thereof, is described in the Examples.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor. By their ability to inhibit neovascularization, the methods of the invention also are effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of angiogenesis inhibitor is typically conducted during or after chemotherapy, although it is preferable to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

Restenosis is a process of smooth muscle cell (SMC) migration and proliferation at the site of percutaneous transluminal coronary angioplasty which hampers the success of angioplasty. The migration and proliferation of SMCs associated with blood vessels during restenosis is related to the process of angiogenesis which is inhibited by the present methods. Therefore, the invention also contemplates inhibition of restenosis by inhibiting angiogenic related processes according to the present methods in a patient following angioplasty procedures. For inhibition of restenosis, the compounds of the invention are typically administered after the angioplasty procedure for from about 2 to about 28 days, and more typically for about the first 14 days following the procedure.

The compounds of the invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, compounds of the invention including polypeptides, and derivatives thereof can be administered intravenously, intraperitoneally, intramuscularly, subcutaneously, intracavity, transdermally, topically, intraocularly, orally, intranasally and can be delivered by peristaltic means.

The compounds of the invention can be administered by administration of a synthetic gene encoding the compounds of the invention, wherein the compounds of the invention are produced when the synthetic gene is expressed.

The therapeutic compositions of this invention are conventionally administered intravenously, for example, by injection of a unit dose. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The dosage ranges for the administration of a compound of the invention depend upon the form of the compound, and its potency, as described further herein, and are amounts large enough to produce the desired effect in which angiogenesis and the disease symptoms mediated by angiogenesis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage also can be adjusted by the individual physician in the event of any complication.

Total daily dose of the compositions of the invention to be administered to a human or other mammal host in single or divided doses may be in amounts, for example, from 0.0001 to 300 mg/kg body weight daily and more usually 1 to 300 mg/kg body weight.

Detection Methods

The compounds of the invention also are suitable for detection of angiogenesis in tissues. The compounds of the invention, once bound to the target tissue can be detected either directly or indirectly. Direct detection can be performed on compounds that comprise a detectable label such as a fluorochrome, a radioactive tag, paramagnetic heavy metal or diagnostic dye.

Alternatively, detection can occur through a secondary interaction. For example, a detectably labeled antibody that recognizes the compound can be used to visualize the location of the compound. One of skill in the art can determine suitable secondary antibodies for use with various compounds.

For in vivo detection, it is preferable to use a detectably labeled compound. The labeled compound is administered to a patient intravenously, intramuscularly, etc. Labels suitable for detection within a patient are particularly preferred. For example, paramagnetically labeled compounds can be detected by magnetic resonance imaging. Radioactively tagged compounds also can be detected.

Examples of specific embodiments of the invention suitable for detection are as follows.

In one embodiment, the invention is a method of detecting angiogenesis in a tissue by contacting the tissue with a compound of the invention, e.g., Pexstatin with said tissue. In this method, for example, said tissue is ex vivo or said tissue is in vivo and said compound is administered intravenously, transdermally, intrasynovially, intramuscularly, intratummorally, intraocularly, intranasally, intrathecally, topically or orally. Alternatively, in this method said compound is conjugated to a fluorochrome, radioactive tag, paramagnetic heavy metal, diagnostic dye or enzyme. In another embodiment of this method, the step of contacting the peptide with the tissue comprises administration of a synthetic gene encoding the peptide to the tissue, wherein the peptide is produced in the tissue when the synthetic gene is expressed therein.

Other Applications

The invention also provides for methods for detecting the compounds of the invention. Thus, in one embodiment, the invention provides a method for detecting a peptide of the invention in a sample, comprising contacting the sample with a compound that binds to and forms a complex with the peptide for a period sufficient to form a complex; and detecting the complex, so that if a complex is detected a peptide of the invention is detected. In such embodiments, the compound that binds with the peptide of the invention can be an antibody.

Additionally, the peptides of the invention may be used for the development of affinity columns for isolation of receptors relevant to the antiangiogenic activity of the peptide of the invention. As is known in the art, isolation and purification of a receptor may be followed by amino acid sequencing to identify and isolate polynucleotides which encode the receptor. This permits use of recombinant expression of the receptor to produce large amounts of the receptor, e.g., for use in high throughput screening assays to identify other angiogenesis inhibitors.

The peptides of the present invention may be chemically coupled to isotopes, enzymes, carrier proteins, cytotoxic agents, fluorescent molecules, chemiluminescent, bioluminescent and other compounds for a variety of applications. For example, a peptide may be labeled to facilitate testing of its ability to bind antisera or to detect cell types which possess a relevant receptor. The coupling technique is generally chosen on the basis of the functional groups available on the amino acids of the peptide including, but not limited to amino, sulfhydral, carboxyl, amide, phenol, and imidazole groups. Various reagents used to effect such couplings include among others, glutaraldehyde, dizodized benzidine, carbodiimide, and p-benzoquinone.

The efficiency of the coupling reaction is determined using different techniques appropriate for the specific reaction. For example, radiolabeling of the peptide with $I^{125}$ may be accomplished using chloramine T and $NaI^{125}$ of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, a labeled peptide may be obtained which is free from unreacted $NaI^{125}$.

Kits for measurement of the compounds of the invention are also contemplated as part of the present invention. Antisera that possess the highest titer and specificity and can detect the peptides of the invention in extracts of plasma, urine, tissues, and in cell culture media may be used to establish assay kits for rapid, reliable, sensitive, and specific measurement and localization of peptides of the invention. These assay kits may employ (but are not limited to) the following techniques: competitive and non-competitive assays, radioimmunoassay (RIA), bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established by means well known to those skilled in the art.

The above described assay kit would provide instructions, antiserum, one or more peptides of the invention, and possibly radiolabeled peptides of the invention and/or reagents for precipitation of bound peptide/antibody complexes. Such a kit would be useful for the measurement of the peptide of the invention in biological fluids and tissue extracts of animals and humans with and without tumors, as is well known in the art.

Also contemplated is a kit that may be used to visualize or localize the peptide of the invention in tissues and cells. Immunohistochemistry techniques and kits, for example, which employ such techniques are well known to those of ordinary skill in the art. Such a kit provides antisera to the peptide of the invention, and possibly blocking serum and secondary antiserum linked to a fluorescent molecule such as fluorescein isothiocyanate, or to some other reagent used to visualize the primary antiserum. Using this methodology, biopsied tumors may be examined for sites of peptide production or for sites of the peptide receptor. Alternatively, a kit may supply radiolabeled nucleic acids for use in in situ hybridization to probe for messenger RNA which encodes the compounds of the invention.

All references cited herein are incorporated by reference in their entirety.

EXAMPLES

Example 1

Effects of Systemic Administration of Pexstatin Peptide on Melanoma Tumor Growth in the Chick Embryo CS-1 melanoma tumor cells ($5 \times 10^6$) were inoculated on the Chorioallantoic Membranes (CAMs) of 10 day old chick embryos. Twenty four hours later the embryos received a single intravenous injection of 50 μg of Pexstatin peptide or PBS control. At the end of a 7 day incubation period the resulting tumors were resected and wet weights determined. The results are shown in FIG. 1. Data bars represent the mean±the standard errors of the tumor weight from 5 to 10 embryos per condition.

Conclusions: As can be seen in FIG. 1, Systemic administration of Pexstatin inhibited CS1 melanoma tumor growth by approximately 60% within 7 days as compared to controls. These experiments were repeated 2 to 3 times with similar results. Moreover, no toxic side effects were noted during the assay period. These findings suggest that Pexstatin is a potent anti-tumor peptide in this animal model.

Example 2

Figure 2:
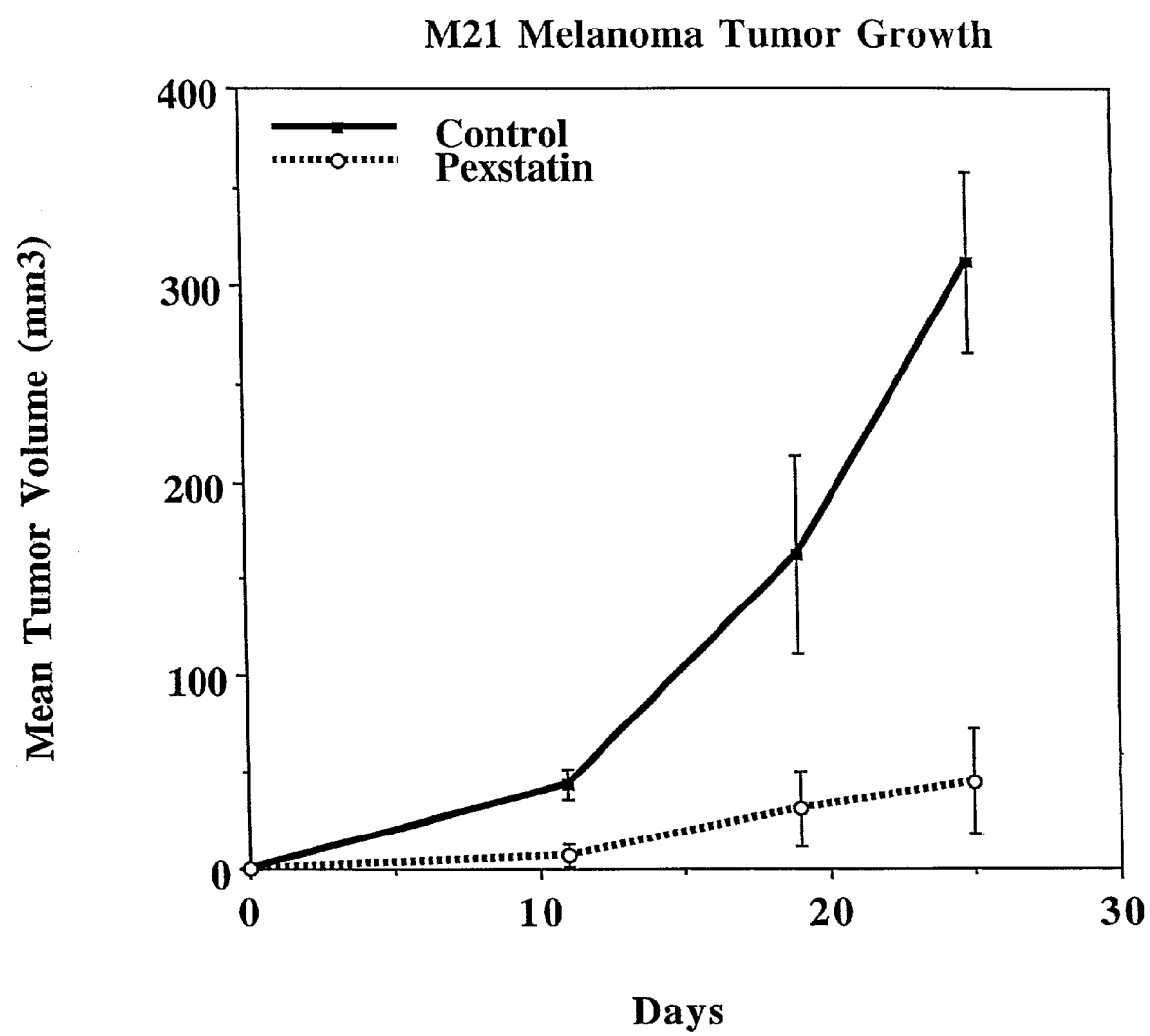
FIG. 2 shows the effects of systemic administration of Pexstatin on melanoma tumor growth in nude mice.

Effects of Systemic Administration of Pexstatin Peptide on Melanoma Tumor Growth in Nude Mice M21 human melanoma tumor cells ($2 \times 10^6$) were injected subcutaneously into female nude mice. Twenty four hours later the mice were treated daily with injections of 100 μg of Pexstatin MMP-2 peptide or PBS controls. Tumor sizes were monitored daily by caliper measurements. The results of the experiments are shown in FIG. 2. Data bars represent the mean tumor volume+the standard errors at each time point. Tumor volumes were estimated using the formula $V=L2 \times W/2$, V=volume, L=length, and W=width.

Conclusions: FIG. 2 shows that systemic administration of Pexstatin potently inhibited human M21 melanoma tumor growth by approximately 80 to 90% as compared to controls. These experiments were repeated 2 times with similar results. Moreover, no toxic side effects were noted during the assay period. These findings suggest that Pexstatin is a potent antitumor peptide in this animal model.

Example 3

Effects of Systemic Administration of Pexstatin on Angiogenesis in vivo

Figure 3:
FIG. 3 shows the effects of systemic administration of Pexstatin on angiogenesis in vivo.
Figure 3:
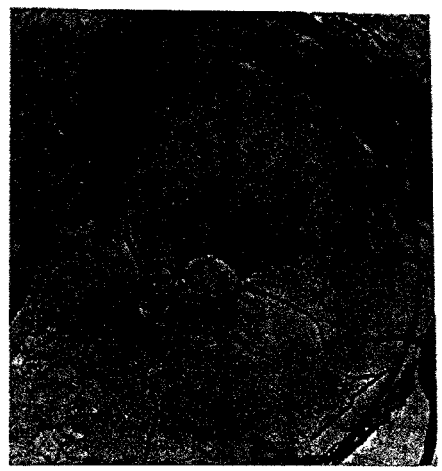
Figure 3:
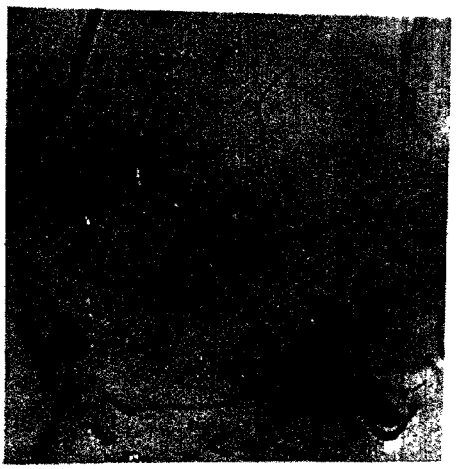
Figure 3:

A). Filter discs saturated with βFGF were placed on the CAMs of 10 day old chick embryos. Twenty four hours later, the embryos received a single intravenous injection with 50 μg of Pexstatin, control peptide or PBS. At the end of a 3 day incubation period the filter discs and surrounding CAM tissue were removed and angiogenesis was quantified by counting the number of blood vessel branch points within the area of the filter disc. FIG. 3 shows examples of CAM tissue from a typical experiment.

Figure 4:
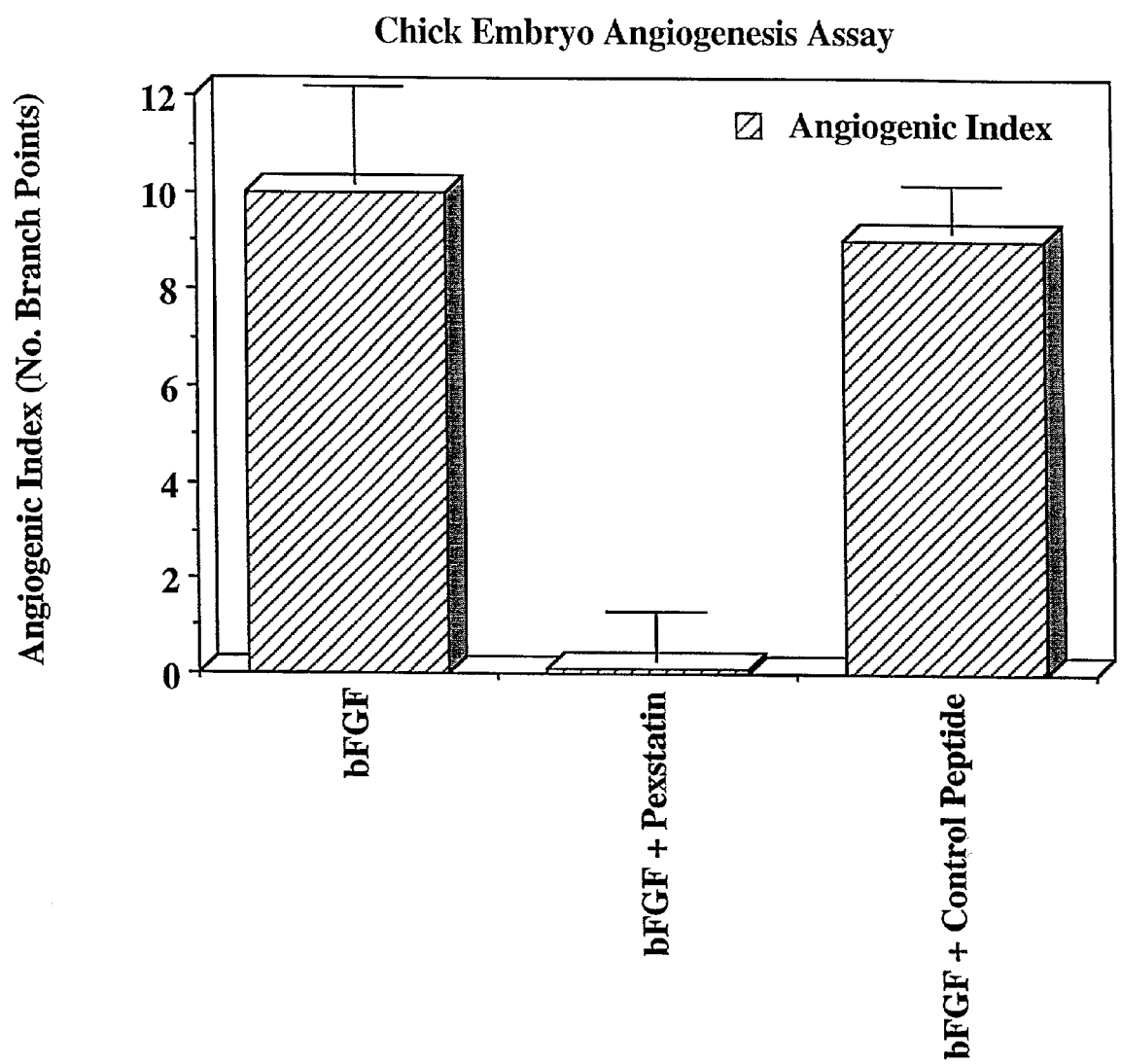
FIG. 4 is a bar chart of the angiogenesis index for experiments which examined the effects of systemic administration of Pexstatin on angiogenesis in vivo

B). FIG. 4 illustrates the quantification of the angiogenesis experiment with Pexstatin. Data bars represent the mean+standard errors of 5 to 10 embryos per condition. The angiogenesis index is equal to the number of branch points from experimentally treated embryos minus the number of branch points from CAMs in the absence of βFGF.

Conclusions: As shown by FIG. 4, systemic administration of 50 μg of Pexstatin inhibited βFGF induced angiogenesis by approximately 90% as compared to controls. Importantly, no toxic side effects were noted in the embryos during the assay period. Moreover, little if any effect from this peptide fragment of MMP-2 was noted on normal quiescent blood vessels.

Example 4

Effects of Pexstatin on B16 Melanoma Tumor Metastasis in vivo

Figure 5:
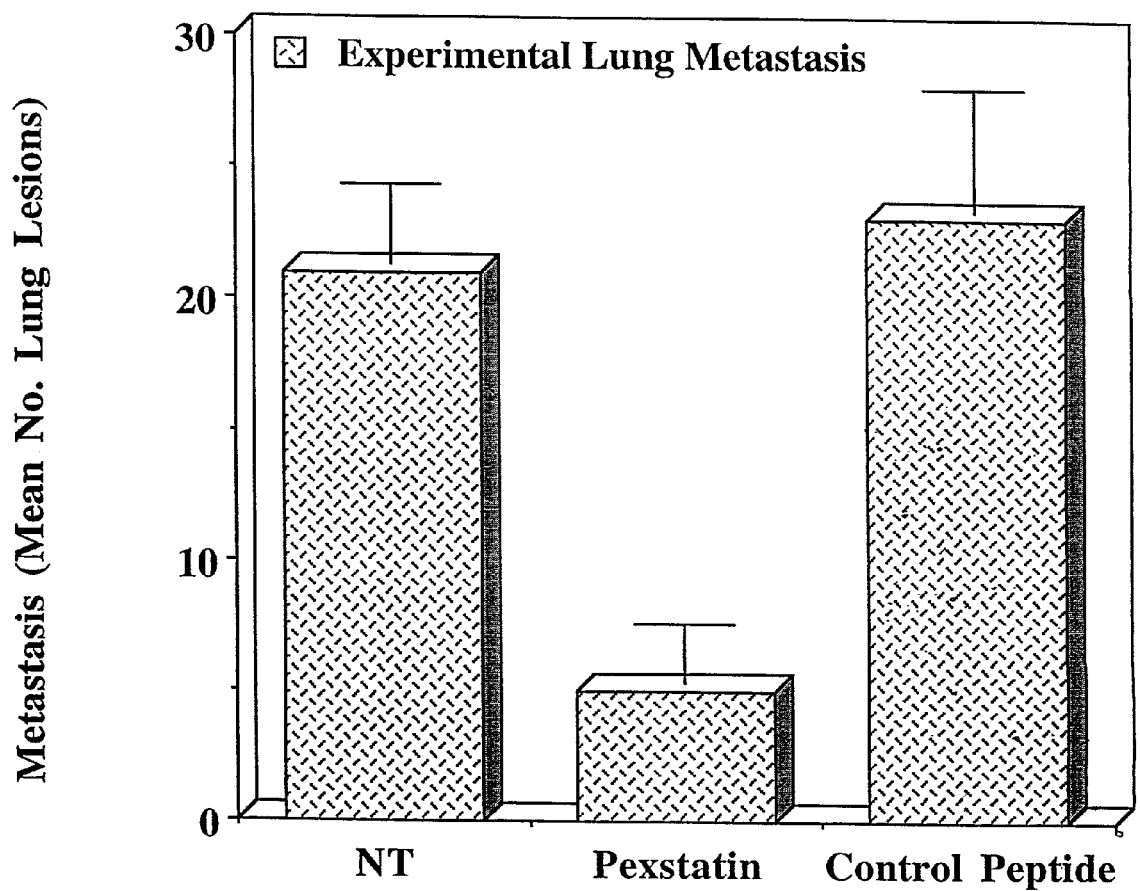
FIG. 5 shows the effects of Pexstatin on B 16 melanoma tumor metastasis in vivo.

To examine the effects of Pexstatin on melanoma tumor metastasis in vivo, the chick embryo experimental metastasis model was utilized. Briefly, B16 melanoma tumor cells ($2.5 \times 10^4$) were inoculated intravenously with Pexstatin (10 μg/embryo) or a control peptide in 12 day old chick embryos. In addition, a no treatment control was also added (NT). The Embryos were allowed to incubate for a total of 7 days. At the end of a 7 day incubation period the embryos were sacrificed and the lungs were removed for analysis. The number of melanoma lung lesions were counted for each lobe of the lung. The results are shown in FIG. 5. Data bars represent the mean+the standard errors of the metastatic lung lesions from 5 to 10 embryos per condition.

Conclusions: FIG. 5 shows that Pexstatin inhibited experimental B16 melanoma metastasis by approximately 80% as compared to controls. In fact, in some of the embryos, little, if any, tumor could be detected. Since experimental metastasis is unlikely to involve angiogenesis, these results indicate that Pexstatin can have an effect on tumor cell invasion as well as endothelial cell invasion. Taken together, these findings demonstrate a potently antimetastatic effect of Pexstatin in vivo, providing further evidence for the utility of the Pexstatin peptide in human clinical applications.

Example 5

Schematic Representation of the Relative Location of Pexstatin Within Intact MMP-2

The crystal structural of intact MMP-2 has been determined. FIG. 6 shows the relative location of Pexstatin (amino acids 582–590) within loop like structures of the hemopexin domain of MMP-2. Pexstatin is indicated as item 1 on the Figure.

All of the publications which are cited in the body of the instant specification are hereby incorporated by reference in their entirety.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

What is claimed is:

1. An isolated anti-angiogenic peptide comprising the sequence of SEQ ID NO: 2.
2. The peptide of claim 1 wherein said peptide inhibits angiogenesis.
3. The peptide of claim 1 wherein said peptide inhibits metastasis.
4. The peptide of claim 1 wherein said peptide inhibits an angiogenic disease.
5. The peptide of claim 4 wherein the disease is psoriasis, macular degeneration, a neurological disease, or restenosis in a tissue.
6. An isolated peptide consisting of the sequence in SEQ ID No: 1.
7. An peptide of The claim 1 consisting of SEQ ID No: 2.

* * * * *

UNITED STATES PATENT AND TRADEMARK OFFICE
CERTIFICATE OF CORRECTION

PATENT NO. : 7,019,108 B2 Page 1 of 1
APPLICATION NO. : 09/872165
DATED : March 28, 2006
INVENTOR(S) : Peter Brooks and Dorothy Rodriguez It is certified that error appears in the above-identified patent and that said Letters Patent is hereby corrected as shown below:

In column 1, line 9, cancel the text beginning with "R29CA 74132-01" and ending with "Institute" in line 10, and insert the following: --CA074132 awarded by the National Institutes of Health. The government has certain rights in the invention.--

Signed and Sealed this

Ninth Day of June, 2009

JOHN DOLL
*Acting Director of the United States Patent and Trademark Office*